United States Patent [19]

Piekarski et al.

[11] 4,036,867
[45] July 19, 1977

[54] ORGANO-ALUMINUM-SILICON REDUCING AGENTS AND PROCESS

[75] Inventors: Gottfried Piekarski, Burghausen; Anton Hundmeyer, Burghausen; Dieter Kippe, Burghausen; Siegmund Maier, Emmerting, all of Germany

[73] Assignee: Wacker-Chemie GmbH, Munich, Germany

[21] Appl. No.: 561,026

[22] Filed: Mar. 24, 1975

[30] Foreign Application Priority Data

Mar. 27, 1974 Germany .......................... 2414875

[51] Int. Cl.² .............................................. C07F 5/06
[52] U.S. Cl. ........................... 260/448 A; 252/431 R
[58] Field of Search ............... 260/448 A, 448 R, 448; 252/429 B, 431 R

[56] References Cited

U.S. PATENT DOCUMENTS

| 2,961,453 | 11/1960 | Sleddon | 260/448 A |
| 3,444,227 | 5/1969 | Roberts et al. | 260/448 R |
| 3,755,274 | 8/1973 | Piekarski et al. | 252/429 B |
| 3,787,323 | 1/1974 | Aiskima et al. | 252/429 B |

OTHER PUBLICATIONS

Chemical Abstracts, V54,10862c, (1960).
Chemical Abstracts, V53,21666g, (1959).
J.A.C.S., V80, pp. 1546–1549, (1958), Kriner et al.
Jenkner, L. Naturf. V14b, pp. 133–134, (1959).
Borison et al., Organosilicon Heteropolymers and Heterocompounds, Plenum Press, N. Y., pp. 274–286, (1970).

Primary Examiner—Helen M. S. Sneed
Attorney, Agent, or Firm—Hammond & Littell

[57] ABSTRACT

Organo-aluminum-silicon reducing agents reaction product of a dialkyl aluminum hydride with a polysiloxane having a viscosity of from 5 to 100 cSt (25° C) and siloxane units having the formula

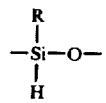

in a molar ratio of from 0.8 to 2 mols of said siloxane units per mol of said dialkyl aluminum hydride, at a temperature not in excess of 80° C, as well as the process of producing reducing agent reaction products. These reducing agent reaction products are soluble in organic solvents and can be used in solution therein.

16 Claims, 1 Drawing Figure

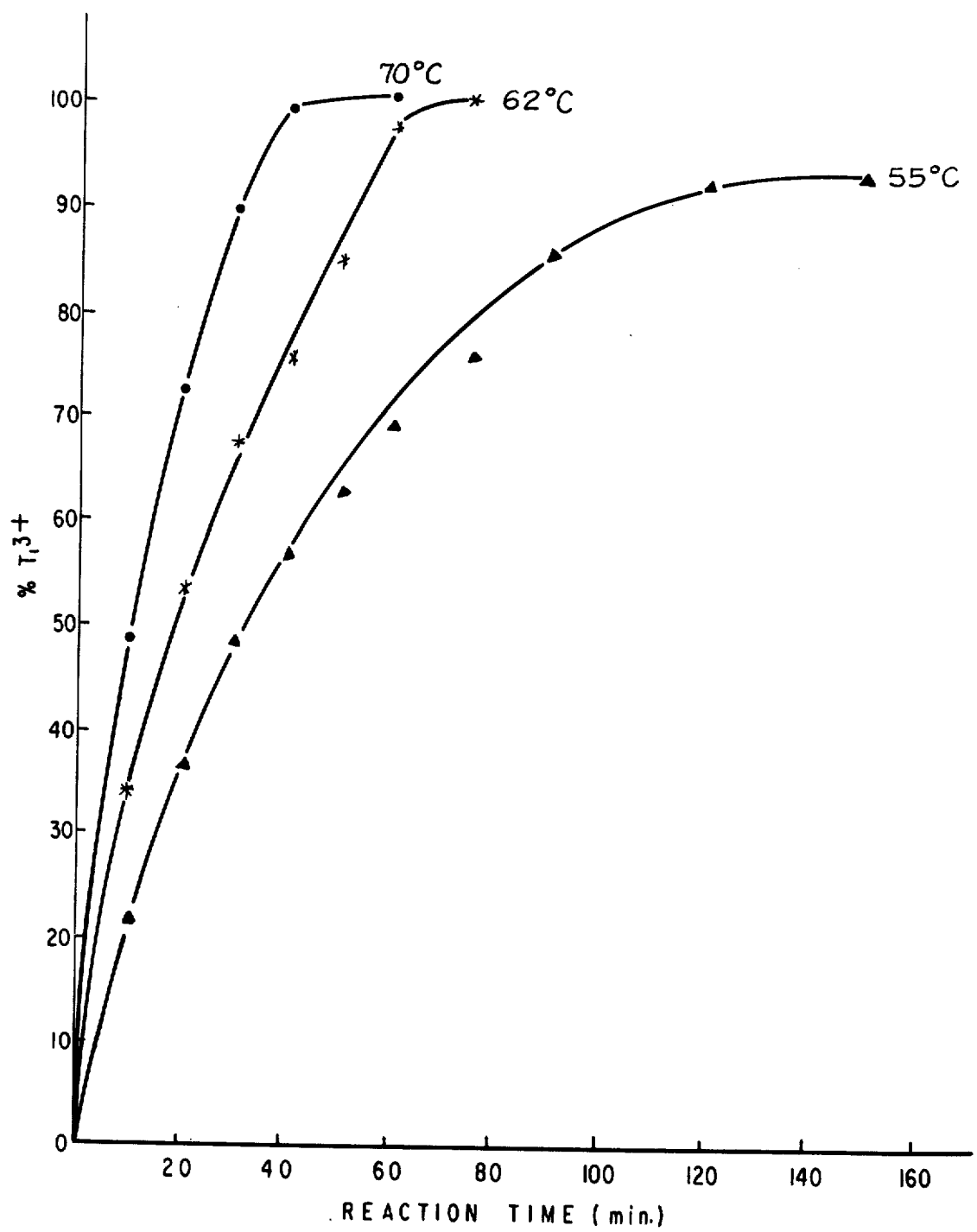

ORGANO-ALUMINUM-SILICON REDUCING AGENTS AND PROCESS

THE PRIOR ART

Various types of reducing agents soluble in organic solvents have previously been disclosed and used. These include silicon compounds containing hydrogen bonded to silicon or metal-organyls with metals of main groups I, II and III of the Periodic System, for example, sodium alkyls, magnesium alkyls, and aluminum alkyls; and alkyl aluminosiloxanes with and without hydrogen bonded to silicon. Literature references to such reducing agents include Ziegler, *Annalen der Chemie* (1959) volume 623, page 9; Reinheckel, *Angewandte Chemie* (1963), volume 75, page 1206; and German Pat. Nos. 954,645; 1,079,600 and 1,936,205.

These reducing agents all have various disadvantages. Thus, for example, certain compounds containing hydrogen bonded to silicon, such as silanes, are either difficult to manufacture or are too volatile to be of much use. Polysiloxanes containing hydrogen bonded to silicon generally require the conjoint use either of catalysts, for example, aluminum chloride, or platinum compounds, or of hydrogen donors, for example, aliphatic alcohols, in order to be effective as reducing agents. Certain metal organyls, for example, triethyl aluminum, are volatile and dangerous to handle, and also have an excessively vigorous uncontrollable reactivity, whereas other metal-alkyls, for example, Grignard compounds, as well as the alkyl aluminosiloxanes mentioned above, often require special, and sometimes expensive, manufacturing procedures.

OBJECTS OF THE INVENTION

An object of the present invention is the development of an organo-aluminum-silicon reducing agent reaction product prepared by the reaction at a temperature of below 80° C of a dialkyl aluminum hydride from 2 to 8 carbon atoms in each of the alkyls, with a hydrogenpolysiloxane having a viscosity of from 5 to 100 cST at 25° C and siloxane units having the formula

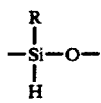

wherein R is a member selected from the group consisting of alkyl having from 1 to 6 carbon atoms, cycloalkyl having from 5 to 6 carbon atoms and phenyl, said hydrogen polysiloxane having the three valences of its silicon atoms on the ends of polysiloxane chain satisfied by R, hydrogen or, at most, one hydroxyl group per end silicon atom, in a molar ratio of from 0.8 to 2 mols of said siloxane per mol of said dialkyl aluminum hydride.

Another object of the present invention is the development of a process for the production of an organo-aluminum-silicon reducing agent consisting essentially of reacting a hydrogenpolysiloxane having a viscosity of from 5 to 100 cST at 25° C and siloxane units having the formula

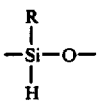

wherein R is a member selected from the group consisting of alkyl having from 1 to 6 carbon atoms, cycloalkyl having from 5 to 6 carbon atoms and phenyl, said hydrogenpolysiloxane having the three valences of its silicon atoms on the ends of polysiloxane chain satisifed by R, hydrogen or, at most, one hydroxyl group per end silicon atom, with a dialkyl aluminum hydride having from 2 to 8 carbon atoms in each of the alkyls, at a temperature not exceeding 80° C and in a molar ratio of from 0.8 to 2 mols of said siloxane per mol of said dialkyl aluminum hydride, and recovering said organo-aluminum reducing agent.

These and other objects of the invention will become more apparent as the description thereof proceeds.

THE DRAWING

The FIGURE is a graph of rate of reduction with the reducing agent of the invention at various temperatures.

DESCRIPTION OF THE INVENTION

It has now been found that a reducing agent can be produced by a process of reducing a hydrogenpolysiloxane containing siloxane units of the general formula

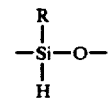

in which R denotes an alkyl group having up to 6 carbon atoms an aryl group, such as phenyl, or a cycyloalkyl group, having the three valences of the terminal silicon atoms at the end of the chain satisfied by groups within the definition of R and/or hydrogen, and/or by not more than one hydroxy group per silicon atom, and having a viscosity of from 5 to 100 cSt at 25° C, with a dialkyl aluminum hydride, the alkyl moieties of which each have from 2 to 8 carbon atoms, at a temperature not exceeding 80° C, and in a molar ratio of from 0.8 to 2, preferably from 1 to 1.2 mols of siloxane units per mol of dialkyl aluminum hydride. Advantages of this process are that it does not have to be carried out in a pressure vessel, that the reaction takes place practically quantitatively and fairly quickly, and that no solvent is necessary.

More particularly, the invention resides in a process for the production of an organo-aluminum-silicon reducing agent consisting essentially of reacting a hydrogenpolysiloxane having a viscosity of from 5 to 100 cSt at 25° C and siloxane units having the formula:

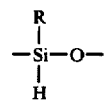

wherein R is a member selected from the group consisting of alkyl having from 1 to 6 carbon atoms, cycloalkyl having from 5 to 6 carbon atoms and phenyl, said hydrogenpolysiloxane having the three valences of its silicon atoms on the ends of polysiloxane chain satisfied by R, hydrogen or, at most, one hydroxyl group per end silicon atom, with a dialkyl aluminum hydride having from 2 to 8 carbon atoms in each of the alkyls, at a temperature not exceeding 80° C and in a molar ratio of from 0.8 to 2 mols of said siloxane per mol of said dialkyl aluminum hydride, and recovering said organoaluminum reducing agent; as well as an organoaluminum-silicon reducing agent reaction product prepared at a temperature of below 80° C by the reaction of a dialkyl aluminum hydride having from 2 to 8 carbon atoms in each of the alkyls, with a hydrogenpolysiloxane having a viscosity of from 5 to 100 cSt at 25° C and siloxane units having the formula

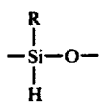

wherein R is a member selected from the group consisting of alkyl having from 1 to 6 carbon atoms, cycloalkyl having from 5 to 6 carbon atoms and phenyl, said hydrogenpolysiloxane having the three valences of its silicon atoms on the ends of polysiloxane chain satisfied by R, hydrogen or, at most, one hydroxyl group per end silicon atom, in a molar ratio of from 0.8 to 2 mols of said siloxane per mol of said dialkyl aluminum hydride.

The reaction between the hydrogenpolysiloxane and the dialkyl aluminum hydride starts exothermically at 20° C or even less. It can be easily controlled by cooling the reactant mixture and/or by controlling the rate at which the two reactants are brought together. The reaction is preferably carried out at from 50° to 65° C. It can be carried out at normal pressure, and generally takes from 1 to 3 hours.

Trialkyl aluminum compounds generally react with hydrogenpolysiloxanes only at relatively high temperatures, which has the disadvantages, first that if too low a temperature is used there is an accumulation of unreacted reactants, especially when using large batches, which could result in a spontaneous and uncontrollable reaction, and secondly that if too high a temperature is used, increasingly great amounts of gaseous decomposition products are formed. In contrast to this, the dialkyl aluminum hydrides used according to the present invention will react with hydrogenpolysiloxanes at lower temperatures, which has the advantages both that much smaller amounts of gaseous products are formed, and that there is less danger of accumulating unreacted reactants.

The reactants can be carried out either discontinuously or continuously, for example, by means of a cascade arrangement.

The exact course of the reaction is not known, but it is thought that the reaction takes place primarily according to the following reaction equation:

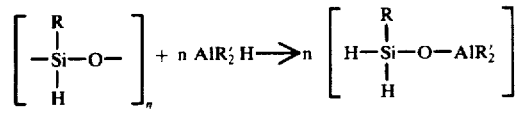

in which R is defined as above, R' denotes an alkyl group having from 2 to 8 carbon atoms, and n denotes an integer of at least 2. The reaction products are slightly viscous liquids, which are free of dialkyl aluminum hydrides and which do not ignite spontaneously. They contain various by-products in addition to the products shown in the above equation.

Suitable hydrogenpolysiloxanes for use in the present process include, for example, methylhydrogenpolysiloxanes (suitably having a viscosity of from 20 to 40 cSt at 25° C), ethylhydrogenpolysiloxanes (suitably having a viscosity of from 25 to 40 cSt at 25° C), and phenylhydrogenpolysiloxanes (suitably having a viscosity of from 45 to 70 cSt at 25° C), the siloxane chain of all of which are, for the most part, end-blocked with trimethylsilyl groups. Cyclic hydrogenpolysiloxanes are also suitable, for example, methylhydrogencyclotrisiloxane, and methylhydrogencyclotetrasiloxane. Commercially available methylhydrogenpolysiloxanes are quite suitable; these generally have a viscosity of from 25 to 35 cSt at 25° C, and, for the most part, are end-blocked with trimethylsilyl groups, with the remainder being hydroxy groups in a content of from 0.05 to 0.2% by weight, preferably 0.1% by weight.

The dialkyl aluminum hydrides used have alkyl moieties each having from 2 to 8, preferably from 2 to 4, carbon atoms. The two alkyl moieties in the compound may be identical or different. Examples of suitable alkyl moieties are ethyl, n-propyl, isopropyl, n-butyl, isobutyl, 2-ethylhexyl, and n-octyl groups. The preferred dialkyl aluminum hydrides are diethyl aluminum hydride, di-n-butyl aluminum hydride, and di-isobutyl aluminum hydride, which latter compound is easily obtainable industrially.

From the above it can be seen that a preferred reaction is that of a methylhydrogenpolysiloxane having a viscosity of from 25 to 35 cSt at 25° C with a dialkyl aluminum hydride, the alkyl moieties of which each have from 2 to 4 carbon atoms, in a molar ratio of from 1 to 1.2 mols of siloxane units per mol of dialkyl aluminum hydride.

The reducing action of the organo-aluminum-silicon compounds obtained by the present process is due to the presence of both aluminum alkyl groups and of silicon-hydrogen groups in the molecule, which results in such advantages as a higher reducing capacity and a greater reactivity as compared with hydrogenpolysiloxanes. These products also have advantages discussed previously over those manufactured with trialkyl aluminum. The products can be used for a variety of reductions in both aliphatic and aromatic solvents, preferably in aliphatic hydrocarbons. Halogenated hydrocarbons, for example, carbon tetrachloride, and ethers, for example, di-n-butyl ether and tetrahydrofuran, can be of advantage in certain reductions and can be used as solvents for the present products. In contrast thereto, triethyl aluminum is not inert to chlorinated hydrocarbons (see Reinheckel loc. city.).

The reducing agents of the invention are particularly suitable for the reducing of metal compounds, for example, compounds of the metals of groups IV to VII of the Periodic System. This is of particular industrial importance since such reduction yields finely-divided higher active suspensions of the corresponding low-valency metal compounds or of the metals themselves, which, optionally after elution with inert solvents, can be used as catalysts in various reactions, for example, in hydrogenation, addition, polymerization or even further reduction reactions.

Compounds of metals of sub-groups IV to VI of the Periodic System are used as reduction catalysts in the polymerization of ethylene and other α-olefins, and in these reactions it is important to obtain an optimum ratio of the individual valencies of the particular metals used. The reducing agents of the invention are useful for obtaining such an optimum ratio, since, for example, by using these reducing agents it is possible, by suitable choice of reaction conditions, such as time, temperature, and dilution, to obtain any desired degree of reduction of titanium tetrachloride, as determined by the percentage of $Ti^{3+}$. Likewise chromium compounds, for example, chromium trioxide, and chromium oxychloride $CrO_2Cl_2$, can be reduced selectively to the requisite valency or valency combination which exhibits the highest polymerization activity. Such selective reduction is not possible when using triethyl aluminum or diethyl aluminum hydride as the reducing agent. When using these latter reducing agents, chromium compounds showing no catalytic polymerization activity are obtained.

A process for the manufacture of low-pressure polyethylene using a polymerization catalyst that is a reaction product of a reducing agent manufactured according to the present invention with certain titanium and vanadium compounds is described and claimed in our copending U.S. application Ser. No. 561,045, filed concurrently herewith, now U.S. Pat. No. 3,991,259.

The following specific embodiments are illustrative of the invention without being limitative in any respect.

EXAMPLES

The following Examples 1 to 6 illustrate the process of the invention and Example 7 illustrates the use of a product according to the invention for the reduction of titanium. All of the organohydrogenpolysiloxanes used in the examples were end-blocked with trimethylsilyl groups. The molar amounts given for the polysiloxanes refer to siloxane units.

EXAMPLE 1

79.0 gm (917 mmols) of diethyl aluminum hydride were introduced, under a nitrogen atmosphere, into a 250 ml three-necked flask equipped with a dropping funnel, thermometer, and magnetic stirrer. The dropwise addition of 55.2 gm (917 mmols) of methylhydrogenpolysiloxane having a viscosity of 33 cSt at 25° C was commenced, at a temperature of 24° C. An exothermic reaction commenced immediately. When about 13 gm of the polysiloxane had been added, the temperature had reached 58° C. The temperature was thereafter kept constant at 58° C by cooling and by regulating the speed of the dropwise addition. The total duration of the addition was 90 minutes. After the completion of the dropwise addition, an immediate drop in the exothermic character of the reaction was observed. The reaction mixture was stirred for a further 30 minutes at 58° C, the temperature being maintained by warming. The product was then cooled, and 131.6 gm of a clear low-viscosity liquid, in which no diethyl aluminum hydride was detachable, was obtained. The density of the product was 0.896 gm/cm³ at 20° C.

EXAMPLE 2

79.3 gm (557 mmols) of di-n-butyl aluminum hydride were introduced into the apparatus described in Example 1. The dropwise addition of 33.5 gm (557 mmols) of methylhydrogenpolysiloxane having a viscosity of 29 cSt at 25° C was started at a temperature of 24° C. An exothermic reaction commenced immediately. When the mixture had reached a temperature of 60° C, the mixture was stirred at this temperature for a total of 1 hour. The total reaction time (including the heating-up time) was 95 minutes. 110.3 gm of a slightly viscous liquid, free from dialkyl aluminum hydride, was obtained as the product (98% yield). The density of the product was 0.862 gm/cm³ at 20° C.

EXAMPLE 3

59.3 gm (416 mmols) of diisobutyl aluminum hydride and 26 gm (433 mmols) of methylhydrogenpolysiloxane having a viscosity of 31 cSt at 25° C were reacted as described in Example 1 to give 83.5 gm (97.6% yield) of a colorless slightly viscous reaction product having a density of 0.880 gm/cm³ at 20° C.

On exposure to air, severe decomposition of the product, with fuming but without ignition, occurred. The product dissolved, without reaction, in aliphatic and aromatic hydrocarbons, carbon tetrachloride, di-n-butyl ether, and tetrahydrofuran, giving a clear solution in each case. It proved to be suitable for use as a reducing agent for the reduction of halides of metals of the sub-groups IV to VIII of the Periodic System.

EXAMPLE 4

A cascade apparatus, consisting of 2 successive 500 ml flasks equipped with magnetic stirring, and a collecting vessel, was used for the continuous manufacture of the reaction product from a methylhydrogenpolysiloxane (31 cSt at 25° C) and di-isobutyl aluminum hydride. The liquid volume in the two 500 ml reaction flasks was maintained at 200 ml each by means of built-in overflow devices.

298.8 ml of di-isobutyl aluminum hydride and 101.2 ml of the methylhydrogenpolysiloxane (molar ratio 1:1) were metered per hour from storage vessels into the first reaction flask. The temperature was kept at 60° C by cooling. The dwell time in each cascade stage was a half hour and the total dwell time was accordingly 1 hour. After 6 hours' operation, 975 ml of a colorless, slightly viscous liquid had collected in the collecting vessel. The product was free from di-isobutyl aluminum hydride. It showed the same properties as the reaction product obtained in Example 3.

EXAMPLE 5

86.1 gm of diethyl aluminum hydride (1.0 mol) were introduced, under a nitrogen atmosphere, into the apparatus described in Example 1. The dropwise addition of 74.2 gm of ethylhydrogenpolysiloxane (100 mol of siloxane units) having a viscosity of 35 cSt at 25° C was started. An exothermic reaction commenced immediately. When the reaction temperature had reached 58° C, the speed of the dropwise addition was adjusted so that the temperature remained at 58° C. After 1½ hours, all the polysiloxane had been added. After a further 30 minutes, during which the mixture was kept at 58° C by warming, 155.8 gm of a slightly viscous reaction product, which was free of diethyl aluminum hydride, were obtained. It had a density of 0.910 gm/cm³ at 20° C.

EXAMPLE 6

45 kg of di-isobutyl aluminum hydride (316 mols) were initially introduced under a nitrogen atmosphere into a 100 liter reactor and warmed to 58° C. The metering-in of 19 kg of methylhydrogenpolysiloxane (316 mols) having a viscosity of 33 cSt at 25° C was then commenced, while stirring. The reaction was immediately exothermic. The reactor was cooled by means of a cooling jacket. The temperature difference between the cooling jacket and the reaction mixture was about 6° C. The metering-in of the hydrogenpolysiloxane took 2 hours. When it had been completed, no further exothermicity could be observed. The mixture was then stirred for a further hour at 60° C, after which it was cooled to 20° C.

62.3 kg of a slightly viscous liquid were obtained. This corresponded to a yield of 97.5% relative to the starting materials used. Slight amounts of gaseous materials were detected as by-products. The product had a density of 0.880 gm/cm³ at 20° C. Analysis showed it to contain no diethyl aluminum hydride.

EXAMPLE 7

5 ml of the reaction product of Example 6, namely 21.7 mmols based on the formula

H$_2$Si (CH$_3$) —O— Al [CH$_2$CH(CH$_3$)$_2$]$_2$ were dissolved in 30 ml of isooctane under a nitrogen atomsphere in a small cylindrical vessel equipped with a stirrer. After warming to 55° C, 3.85 ml of titanium tetrachloride (35 mmols) were added rapidly. Reduction started immediately. The reaction was moderately exothermic, but took place evenly and was easy to control, so that the required degree of reduction to Ti³⁺ could easily be selected.

The procedure was repeated using temperatures of 62° and 70° C. The accompanying drawing of the FIGURE shows a plot of the amount of Ti³⁺ formed against the reaction time for the three different reaction temperatures. From this, it can be seen that the desired degree of reduction can easily be selected by suitable choice of reaction temperature and duration.

The reaction products were suitable for use as catalysts for the low-pressure polymerization of ethylene and other α-olefins, as described in our copending U.S. Patent application Ser. No. 561,045, filed concurrently herewith now U.S. Pat. No. 3,991,259.

Analogous use of triethyl aluminum or diethyl aluminum hydride for the reduction of titanium tetrachloride led to spontaneous uncontrollable reaction peaks and to products which contained substantial amounts of Ti²⁺ compounds.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A process for the production of an organo-aluminum-silicon reducing agent consisting essentially of reacting a hydrogenpolysiloxane having a viscosity of from 5 to 100 cST at 25° C and at least two siloxane units having the formula

wherein R is a member selected from the group consisting of alkyl having from 1 to 6 carbon atoms, cycloalkyl having from 5 to 6 carbon atoms and phenyl, said hydrogenpolysiloxane having the three valences of its silicon atoms on the ends of the polysiloxane chain satisfied by R, hydrogen or, at most, one hydroxyl group per end silicon atom, with a dialkyl aluminum hydride having from 2 to 8 carbon atoms in each of the alkyls, at a temperature not exceeding 80° C and in a molar ratio of from 0.8 to 2 mols of said siloxane units per mol of said dialkyl aluminum hydride, and recovering said organo-aluminum reducing agent.

2. The process of claim 1, wherein the reaction is carried out at a temperature of from 50° to 65° C.

3. The process of claim 1, wherein the reaction is carried out continuously.

4. The process of claim 1, wherein the molar ratio of the reactants is from 1 to 1.2 mols of siloxane units per mol of dialkyl aluminum hydride.

5. The process of claim 1, wherein said hydrogenpolysiloxane is a member selected from the group consisting of methylhydrogenpolysiloxane, an ethylhydrogenpolysiloxane, and a phenylhydrogenpolysiloxane, each end-blocked with trimethylsilyl groups, and methylhydrogencyclotrisiloxane, and methylhydrogencyclotetrasiloxane.

6. The process of claim 1, wherein said hydrogenpolysiloxane is methylhydrogenpolysiloxane mainly end-blocked with trimethylsilyl groups, having a hydroxy-group content of, at the most, from 0.05 to 0.2% by weight, and having a viscosity of from 25 to 35 cSt at 25° C.

7. The process of claim 1 wherein said dialkyl aluminum hydride has from 2 to 4 carbon atoms in the alkyls.

8. The process of claim 1, wherein said dialkyl aluminum hydride is a member selected from the group consisting of diethyl aluminum hydride, di-n-butyl aluminum hydride, and di-isobutyl aluminum hydride.

9. The process of claim 4, wherein a methylhydrogenpolysiloxane having a viscosity of from 25 to 35 cSt at 25° C is reacted with a dialky aluminum hydride, having from 2 to 4 carbon atoms in the alkyls.

10. An organo-aluminum-silicon reducing agent reaction product prepared by the reaction, at a temperature of below 80° C, of a dialkyl aluminum hydride having from 2 to 8 carbon atoms in each of the alkyls, with a hydrogenpolysiloxane having a viscosity of from 5 to 100 cST at 25° C and at least two siloxane units having the formula

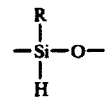

wherein R is a member selected from the group consisting of alkyl having from 1 to 6 carbon atoms, cycloalkyl having from 5 to 6 carbon atoms and phenyl, said hydrogenpolysiloxane having the three valences of its silicon atoms on the ends of the polysiloxane chain satisifed by R, hydrogen or, at most, one hydroxyl group per end silicon atom, in a molar ratio of from 0.8 to 2 mols of said siloxane units per mol of said dialkyl aluminum hydride.

11. The organo-aluminum-silicon reducing agent reaction product of claim 10 wherein the molar ratio of the reactants is from 1 to 1.2 mols of siloxane units per mol of dialkyl aluminum hydride.

12. The organo-aluminum-silicon reducing agent reaction product of claim 10 wherein said hydrogenpolysiloxane is a member selected from the group consisting of methylhydrogenpolysiloxane, an ethylhydrogenpolysiloxane, and a phenylhydrogenpolysiloxane, each end-blocked with trimethylsilyl groups, and methylhydrogencyclotrisiloxane, and methylhydrogencyclotetrasiloxane.

13. The organo-aluminum-silicon reducing agent reaction product of claim 10 wherein said hydrogenpolysiloxane is methylhydrogenpolysiloxane mainly end-blocked with trimethylsilyl groups, having a hydroxy-group content of, at the most, from 0.05 to 0.2% by weight, and having a viscosity of from 25 to 35 cSt at 25° C.

14. The organo-aluminum-silicon reducing agent reaction product of claim 10 wherein said dialkyl aluminum hydride has from 2 to 4 carbon atoms in the alkyls.

15. The organo-aluminum-silicon reducing agent reaction product of claim 10 wherein said dialkyl aluminum hydride is a member selected from the group consisting of diethyl aluminum hydride, di-n-butyl aluminum hydride, and di-isobutyl aluminum hydride.

16. The organo-aluminum-silicon reducing agent reaction product of claim 11 wherein a methylhydrogenpolysiloxane having a viscosity of from 25 to 35 cSt at 25° C is reacted with a dialkyl aluminum hydride, having from 2 to 4 carbon atoms in the alkyls.

* * * * *